United States Patent [19]

van den Brink et al.

[11] 4,028,418

[45] June 7, 1977

[54] PROCESS FOR THE PREPARATION OF CYCLOBUTANONES

[75] Inventors: Marinus J. van den Brink; Helena Austermühle-Bertola; Petrus A. Kramer, all of Amsterdam, Netherlands

[73] Assignee: Shell Oil Company, Houston, Tex.

[22] Filed: Aug. 25, 1975

[21] Appl. No.: 607,534

[30] Foreign Application Priority Data

May 21, 1975 United Kingdom ............ 21814/75

[52] U.S. Cl. ......................... 260/586 C; 260/345.2; 260/346.2 R; 260/468 H; 260/514 G; 260/514 H; 260/515 R; 260/520 E; 260/586 R; 260/586 G; 260/590 E

[51] Int. Cl.² ................... C07C 45/02; C07C 51/00

[58] Field of Search .................... 260/586 C, 514 H

[56] References Cited

UNITED STATES PATENTS 3,390,185    6/1968    Martin .......................... 260/586 C

FOREIGN PATENTS OR APPLICATIONS 2,417,615   11/1974   Germany ....................... 260/514 H
1,194,604    6/1970   United Kingdom

OTHER PUBLICATIONS

Ghosez I, Tetrahedron, 27, pp. 615–633 (1971).
Brady, I, Synthesis, pp. 415–422 (1971).
Brady, II, J. Org. Chem., 31, pp. 626–628 (1966).
Stevens, J. Am. Chem. Soc., 87, pp. 5257–5259 (1965).
Ghosez II, Tetrahedron Letters, pp. 135–139 (1966).

Primary Examiner—Lorraine A. Weinberger
Assistant Examiner—Michael Shippen

[57] ABSTRACT

Cyclobutanones and cyclobutenones are prepared by contacting a 2-haloacyl halide with an ethylenically unsaturated compound or an alkyne in an inert aprotic solvent at a temperature above 5° C in the presence of zinc and/or tin.

17 Claims, No Drawings

PROCESS FOR THE PREPARATION OF CYCLOBUTANONES

BACKGROUND OF THE INVENTION

1. Field of the Invention

The invention relates to a process for the preparation of a cyclobutanone of the general formula I

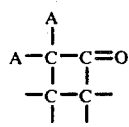
(I)

or of a cyclobutenone of the general formula II

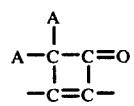
(II)

in which formulas each A represents a halogen atom having an atomic number of not more than 35, a hydrogen atom or a substituted or unsubstituted hydrocarbyl group.

2. Description of the Prior Art

The alpha-halocyclobutanones mentioned in British patent specification No. 1,194,604 are obtained by (2+2)cycloaddition of haloketenes to olefins. This cycloaddition may be effected as described in J.A.C.S. 87 (1965) 5257–9 and Tetrahedron Letters No. 1, pp. 135–9 (1966), by dehydrochlorination of dichloroacetyl chloride with triethylamine. The dichloroketene, formed in situ, reacts with an olefin to give an alpha-chlorocyclobutanone, which, however, is obtained in a low yield, because it reacts with triethylamine with formation of a quaternary ammonium chloride.

The cycloaddition may also be effected as described in J. Org. Chem. 31 (1966) 626–8, by dehalogenation of an alpha-haloacetyl bromide with zinc dust in an inert solvent. The latter article describes the preparation of dichloroketene only, starting from trichloroacetyl bromide and zinc. The dichloroketene is isolated in hydrocarbon solvents such as hexane or octane and the solutions thus obtained are used as source of dichloroketenes (confer the said British patent specification, stating that after undesirable by-products have been removed from the solution of the haloketene the latter is reacted with an olefin). This article fails to reveal anything about the isolation of a monohaloketene prepared from a dihaloacetyl halide and zinc, which suggests that this isolation is impossible, a monohaloketene being an unstable compound, which polymerizes readily, even at very low temperature. This suggestion is fortified by Synthesis, August 1971, pp. 415–22, stating that when monochloroketene is prepared by dehydrohalogenation of monochloroacetyl-chloride with triethylamine in the presence of chloral, a mixture of cis-and trans-4-trichloro-methyl-2-oxetanones is produced, whilst the preparation of monochloroketene by the dehalogenation of dichloroacetyl chloride with zinc in the presence of chloral yields only alpha,beta-dichlorovinyl dichloroacetate. Consequently, the dehydrohalogenation and dehalogenation methods are not equivalent.

Applicant has indeed found that isolation of monochloroketene is impossible, because dichloroacetyl chloride and zinc in diethyl ether form a reaction mixture which does not contain any monochloroketene and which, after removal of the zinc, fails to give any cyclobutanone upon addition of 2,3-dimethyl-2-butene. Surprisingly, it has been found that monochloroketene formed in situ by dehalogenation is capable of entering into a (2+2) cyclo-addition.

SUMMARY OF THE INVENTION

The invention may be defined as relating to a process for the preparation of a cyclobutanone of the general formula I

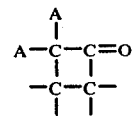
(I)

or of a cyclobutenone of the general formula II

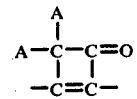
(II)

in which formulas each A represents a halogen atom having an atomic number of not more than 35, a hydrogen atom or a substituted or unsubstituted hydrocarbyl group, which process comprises contacting a 2-haloacyl halide of the general formula

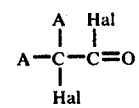
(III)

in which A has the meaning described above and Hal represents a halogen atom having an atomic number of not more than 35, in an inert aprotic polar solvent with an ethylenically unsaturated compound or an alkyne at a temperature above 5° C in the presence of zinc and/or tin.

The process according to the present invention and the 2-haloacyl halide of the general formula III are referred to hereinafter as the novel process and the acyl halide, respectively. The cyclobutanone of the general formula I and the cyclobutenone of the general formula II are together referred to as the cyclic compound. The ethylenically unsaturated compound and the alkyne are together referred to hereinafter as the unsaturated compound.

The ketene formed in situ has the general formula

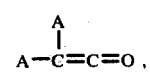
(IV)

in which A has the above-mentioned meaning.

The novel process is preferably conducted with zinc, because this metal usually affords higher yields of cyclic compounds than tin.

The two symbols Hal in the general formula III represent fluorine, chlorine or bromine atoms in any combination.

The two atoms or groups A in the general formula III must remain unaffected during application of the novel process. They may be equal or different. A hydrocarbyl group represented by a symbol A may be an alkyl, a cycloalkyl or an aryl group or a combination thereof. The number of carbon atoms of the hydrocarbyl groups is not critical. Examples of substituted hydrocarbyl groups are hydrocarbyl groups containing halogen atoms or alkoxy groups with, for example, one to six carbon atoms. The alkyl groups may have a straight or a branched chain. The alkyl groups may contain up to, for example, 20 and particularly up to six carbon atoms. The surprising effect mentioned above is particularly exerted by 2,2-dihaloacyl halides. Very good results are usually obtained with 2-haloalkanoyl halides, particularly with 2,2-dihaloalkanoyl halides.

Examples of groups A are methyl, ethyl, propyl, isopropyl, butyl, sec-butyl, tert-butyl, benzyl, phenethyl, trityl, cyclopentyl, cyclohexyl, phenyl, naphthyl, tolyl and xylyl groups. Examples of compounds of the general formula III are monochloroacetyl chloride, dichloroacetyl chloride, trichloroacetyl chloride, 2-chloropropanoyl chloride, 2,2-dichloropropanoyl chloride, 2-chlorobutanoyl chloride, 2,2-dichlorobutanoyl chloride, monochloromonophenylacetyl chloride, dichloromonophenylacetyl chloride, monochloromonocyclohexylacetyl chloride and dichloromonocyclohexylacetyl chloride and the acyl halides obtained when one or more of the chlorine atoms in these compounds are replaced by bromine atoms. Very good results have been obtained with dichloroacetyl chloride.

Ethylenically unsaturated compounds asymmetrical with respect to the double bond may form two different cyclobutanones, and alkynes asymmetrical with respect to the triple bond may form two different cyclobutenones, depending on the regiospecificity of the cycloaddition involved. For an explanation of the concept of "regiospecificity" see "Methoden der Organischen Chemie" (Houben-Weyl), 4th Edition (1971), Vol. IV/4, p. 143.

The unsaturated compounds may be hydrocarbons or may carry non-hydrocarbyl substituents such as, alkoxy, benzyloxy, oxo or ethoxycarbonyl groups, as is the case in, for example, isopropyl 3-methyl-2-butenyl ether, benzyl 3-methyl-2-butenyl ether, ethyl 2,3,5-trimethyl-2,4-hexadienoate and 6-methyl-5-heptene-2-one. However, substituted unsaturated compounds usually give cyclic compounds in relatively low yields, for example, less than 20%, calculated on acyl halide. Unsubstituted unsaturated compounds usually afford the cyclic compounds in a higher yield and are, therefore, preferred. Alkenes are particularly preferred; they usually afford the cyclobutanones in a yield between 50 and 75%. The alkenes may have a straight or a branched chain and may have a cis or trans structure. Examples of alkenes are ethene, propene, 1-butene, cis-2-butene, trans-2-butene, isobutene, 2-pentene, 2-hexene, 3-hexene, 2-heptene, 3-heptene, 2-methyl-2-butene, 3-methyl-2-pentene, 3-methyl-3-hexene, 2,4-dimethyl-3-hexene, 2,3,4-trimethyl-2-pentene, 1-octene, 2-octene, 3-octene, 1-nonene, 1-decene, 1-dodecene, 1-tetradecene, 1-pentadecene, 1-hexadecene, 1-eicosene, 1-docosene, methylene cyclobutane, methylene cyclopentane, methylene cyclohexane, the corresponding isopropylidene cycloalkanes, and 3-phenyl-1-propene. Very good results have been obtained with 2,3-dimethyl-2-butene and 2-methyl-2-pentene.

It has been found that 2,5-dimethyl-2,4-hexadiene reacts stereospecifically with monochloroketene to give trans-2-chloro-4,4-dimethyl-3-(2-methyl-1-propenyl) cyclobutanone and trans-2-chloro-3,3-dimethyl-4-(2-methyl-1-propenyl)cyclobutanone with a very high selectivity. For an explanation of the concept of "stereospecificity" see "Methoden der Organischen Chemie" (Houben-Weyl), 4th Edition (1971), Vol. IV/4, p. 143. The importance of this stereospecificity is explained further below.

Unsaturated compounds containing an allenic structure yield alkylidenecyclobutanones. Examples of allenic un-saturated compounds are allene, 1,2-butadiene, 2,3-pentadiene, 2,4-dimethyl-2,3-pentadiene, 3,5-diethyl-3,4-heptadiene, 5-methyl-1,2-hexadiene, 2,8-dimethyl-4,5-nonadiene, 3-nonyl-1,2-dodecadiene, 1,2-pentadecadiene, allenylbenzene and tetraphenylallene.

When the ethylenically unsaturated compound is a (hetero)cyclic compound, bicyclic compounds containing a cyclobutanone ring are formed. The starting cyclic compound may be, for example, five-, six-, seven- or eight-membered, may be substituted or unsubstituted and may have a second carbon-carbon double bond. One of the members of the ring may be an oxygen atom. Examples of substituents are halogen atoms not bound to a double-bonded carbon atom in a molecule containing only one carbon-carbon double bond, and alkyl groups. Examples of cyclic unsaturated compounds are cyclohexene, cycloheptene, cyclooctene, 1,2-dimethylcyclopentene, 2-methylcyclohexene, 3-methylcyclohexene, 2,5-dimethylfuran, indene, 2,3-dimethylindene and 2H-3,4-dihydropyran.

Examples of alkynes are propyne, 1-butyne, 2-butyne, 1-pentyne, 2-pentyne, 1-hexyne, 1-heptyne, 1-dodecyne, 2-methyl-1-pentyne, phenylethyne and 3-phenyl-1-propyne.

The double- and triple-bonded carbon atoms in ethylenically unsaturated compounds and alkynes which contain only one double- or triple-bond, respectively, may not carry any deactivating substituents, such as halogen atoms carboxyl or esterified carboxyl groups, because such substituted unsaturated compounds hardly form any cyclic compounds, if at all.

It has been found that the reaction has to be carried out in an inert aprotic polar solvent in order to prevent or to diminish the occurrence of side reactions as much as possible. It has been found that ethers, especially dialkyl ethers and alkanones, especially ketones of which not more than one of the carbon atoms attached to the carbonyl group is quaternary, are very suitable solvents.

It is also possible to perform the reaction according to the present invention in a mixture of inert aprotic polar solvents such as a mixture of di-ethylether and methyl-tert.butyl ketone. Small amounts of inert solvents such as toluene or xylene can also be tolerated.

Examples of dialkyl ethers are diethyl ether, di-n-propyl ether, n-propyl i-propyl ether, diisopropyl ether and di-n-butyl ether. Among the ethers, diethyl ether is preferred, because in this solvent usually the highest yields of cyclic compounds are obtained.

The acyl halide may be applied in any concentration in the dialkyl ether and preferably in a concentration below 1 mol/l of dialkyl ether, because at higher concentrations the yield of cyclic compound decreases with increasing concentration. This concentration is preferably in the range of from 0.1 to 0.6 mol/l.

The unsaturated compound and the acyl halide may be dissolved in any molar ratio in the dialkyl ether. The cyclic compounds are obtained in increasing yields at increasing molar ratios of unsaturated compound to acyl halide; for example, at a molar ratio of 4, this yield has attained a value above 90%. In view of this, the molar ratio is preferably in the range of from 2 to 20 and particularly of from 2 to 10.

Ketones, particularly alkanones, are the most attractive solvents found thus far, because high yields of cyclic compounds are obtained therein at concentrations of the acyl halide far above 1 mol/l. This particularly applies to alkanones which have at least two branches in the carbon skeleton of the molecule and of which not more than one of the two carbon atoms attached to the carbonyl group is quaternary. Diisobutyl ketone and methyl tert.-butyl ketone are preferred. In ketones the acyl halide is partly converted into cyclic compounds and partly into polymers, whilst the balance remains unchanged. The presence of unchanged acyl halide is an advantage of the use of ketones, which is not provided by dialkyl ethers; in the latter solvents the acyl halide is partly converted into cyclic compound and the balance into high-molecular-weight material. In some ketones relatively high amounts of polymeric materials may be formed which originate from the acyl halide or the unsaturated compound or from both. Little or very little polymer is formed in diisobutyl ketone and methyl tert.butyl ketone.

The yield of cyclic compounds decreases according as higher concentrations of the acyl halide in a ketone are applied. These yields, however, are still very high at concentrations up to 15 and particularly up to 10 mol per litre of ketone. In view of this, the acyl halide is preferably applied in a concentration in the range of from 1 to 15 mol, and particularly of from 3 to 10 mol per litre of the ketone. The yield rapidly decreases with increasing concentrations of the unsaturated compound above 15 mol/l, irrespective of the acyl halide concentration, the zinc halide and tin halide formed becoming less and less soluble in the surrounding liquid. At concentrations increasing above 40 mol/l these halides are hardly soluble if at all and, consequently, cyclic compounds are only formed with great difficulties, if at all. The The selectivity to cyclic compounds when using ketones as the solvent is hardly influenced by molar ratios of unsaturated compound to acyl halide increasing above 0.5. In view of this, the said molar ratio is preferably chosen in the range of from 0.5 to 10 particularly of from 1 to 2.

The selectivity to cyclic compound increases with increasing molar ratios of zinc or tin to acyl halide. Therefore, this molar ratio is preferably chosen in the range of from 1 to 10 and particularly of from 1 to 5. Very good selectivities are usually obtained at molar ratios in the range of from 3.5 to 4.5. The selectivity to cyclic compound is also favourably influenced by a homogeneous distribution of the zinc or tin in the liquid.

This selectivity is relatively low when zinc dust — which has a reatively high specific surface area — is used, but is much higher when the zinc particles have a relatively low specific surface area, for example when zinc particles having a largest dimension of at least, say, 0.1 mm are applied. High selectivities have been obtained with particles having a largest dimension between 0.5 and 5 mm.

When the novel process is modified by adopting a temperature not higher than 5° C, no measurable cycloaddition takes place. It has been found that the yield of cyclic compound increases at temperatures increasing above 5° C, reaches a maximum at a temperature in the range of from, usually, 25° C to 60° C, and decreases at temperatures increasing beyond the temperature at maximum yield. In view of this the novel process is preferably conducted at a temperature in the range of from 15° C to 100° C and more preferably of from 25° C to 60° C. Best results are usually obtained when conducting the process at a temperature between 35° C and 50° C.

The contacting may be effected in any desired manner. For example, the acyl halide is added to a stirred suspension of zinc or tin in a solution of the unsaturated compound, either at once or, what is preferred, gradually over a period of, say, up to 5 hours. The acyl halide is best added rather rapidly, over a period of, say, between 0.25 and 0.75 hour. Longer addition times usually lower the yield of cyclic compound. Gradual addition of acyl halide is particularly preferred in the case of 2,2-di-and 2,2,2-trihaloacyl halides, because it favourably influences the selectivity to cyclic compound as these halides form in situ mono- and dihaloketenes, respectively, which are easily converted into undesired high-molecular-weight material. In some cases, however, the cyclo-addition may start suddenly after most or all of the acyl halide has been added, with concomitant evolution of heat and considerable polymer formation. The cycloaddition usually starts immediately and proceeds smoothly without significant build-up of the acyl halide concentration when consecutively a suspension of zinc or tin in a solvent containing less than 25%, preferably 2 to 10%, of the total amount of acyl halide to be used is stirred, unsaturated compound is introduced into the stirred suspension and the balance of the acyl halide is added. The said selectivities are also favourably influenced when zinc or tin is gradually added to a solution of the acyl halide and the unsaturated compound or, particularly, when the acyl halide and the unsaturated compound are added together to a stirred suspension of zinc or tin in a solvent.

The selectivity to the cyclobutanones or cyclobutenones is usually improved when the novel process is conducted in the presence of an inorganic halide. Catalytic amounts of such halides are very suitable, preferably in the range of from 0.1 to 10% mol, calculated on 2-haloacyl halide. Very suitable inorganic halides are mercuric iodide, sodium chloride, and particularly potassium iodide and ammonium chloride.

The cyclic compounds prepared by the novel process may be isolated in pure form by distillation of the reaction mixture after removal of the zinc or tin and washing with water to remove the zinc or tin halide obtained. When the cyclic compounds are 2-halocyclobutanones, the reaction mixture may, after removal of the zinc or tin, and their halides, be heated with water in the presence of a base, to effect ring contraction with formation of salts of cyclopropanecarboxylic acids of the general formula

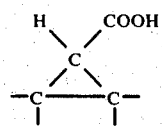 V which are often obtained in a yield of 90–100%, calculated on 2-halocyclobutanone. Substituted cyclopropanecarboxylic esters are particularly suitable for use as insecticides, because they combine a high insecticidal activity with a low mammalian toxicity.

Thus, the present invention relates also to a process for the preparation of cyclopropane carboxylic acids of the general formula V by preparing a compound of the general formula I or II by reacting a 2-haloacyl halide of the general formula III in an inert aprotic polar solvent with an ethylenically unsaturated compound or an alkyne at a temperature above 5° C in the presence of zinc and/or tin and heating the compound(s) obtained with water in the presence of a base and converting the salt of the cyclopropane carboxylic acid obtained into the free acid.

For example, as stated hereinbefore, 2,5-dimethyl-2,4-hexadiene can be reacted with monochloroketene formed in situ with formation of 2-chloro-4,4-dimethyl-3-(2'-methyl-1'-propenyl)cyclobutanone and 2-chloro-3,3-dimethyl-4-(2'-methyl-1'-propenyl)cyclobutanone. The latter two compounds are converted by the above-mentioned ring contraction process into a mixture of salts of cis- and trans-chrysantemummonocarboxylic acid (2,2-dimethyl-3-isobutenylcyclopropanecarboxylic acid), which can be easily converted into the free acid. About 96% of the chrysantemummonocarboxylic acid formed has the trans structure, which constitutes an attractive feature, because trans-chrysantemummonocarboxylic acid has a considerable higher insecticidal activity than cis-chrysantemummonocarboxylic acid.

When 2,4-dimethyl-2,3-pentadiene is reacted with monochloroketene formed in situ, 2-chloro-3,3-dimethyl-4-isopropylidenecylcobutanone and 2-chloro-4,4-dimethyl-3-isopropylidenecyclobutanone are formed. The latter two compounds are converted by the afore-mentioned ring contraction process into salts of 2,2-dimethyl-3-isopropylidenecyclopropanecarboxylic acid.

The cyclopropanecarboxylic acids may be precipitated from the aqueous solutions of their salts by addition of an aqueous solution of a strong mineral acid. The precipitated carboxylic acid obtained when subjecting a 2-halocyclobutanone to the ring contraction/conversion process has a higher purity and a lighter colour when less polymer is concomitantly formed in the novel process. Therefore, methyl tert.butyl ketone and diisobutyl ketone are the preferred solvents when 2-halocyclobutanones are prepared as a precursor of cyclopropanecarboxylic acids.

The cyclobutenones may be hydrogenated to the corresponding cyclobutanones, which may be used as described hereinbefore.

The invention is further illustrated by means of the following examples. The experiments described were conducted in a three-necked flask, provided with a paddle stirrer, a dosage funnel with cock, a thermometer, an inlet for nitrogen and a water-cooled reflux condenser provided with a drying tube. The experiments were carried out under nitrogen.

Some of the compounds according to the formulas I, II or V are novel compounds.

The experiments described in Examples I–V were conducted as follows, unless otherwise stated.

The flask was charged with 2,3-dimethyl-2-butene, zinc granules and 1 l of dried diethyl ether. The zinc granules had a largest dimension of 1 mm. The suspension in the flask was kept boiling under reflux, dichloroacetyl chloride was admitted dropwise from the dosage funnel over a period of 4 hours and the reaction mixture thus formed was stirred under reflux for an additional period of 8 hours. Throughout the experiments the stirrer kept the zinc homogeneously distributed in the liquid. The dichloroacetyl chloride was fully converted, partly into 2-chloro-3,3,4,4-tetramethylcyclobutanone — hereinafter referred to as "compound A" — and the balance into high-molecular-weight products. The 2,3-dimethyl-2-butene that had reacted was fully converted into compound A. The yield of compound A is calculated on starting dichloroacetyl chloride. The compounds 2,3-dimethyl-2-butene and dichloroacetyl chloride are referred to as DMB and DCAC, respectively, and their concentrations are expressed in mol per liter of solvent.

EXAMPLE I

Five experiments were conducted, using the concentrations of DMB and DCAC and the molar ratios of zinc to DCAC stated in Table I. This table also gives the calculated molar ratios of DMB to DCAC and presents the yields of compound A.

Table I

| Experiment No. | Concentration, DMB | Mol/l, of DCAC | Molar ratio DMB:DCAC | Molar ratio Zn:DCAC | Yield of A, % |
|---|---|---|---|---|---|
| 1 | 0.24 | 0.77 | 0.31 | 9.2 | 22 |
| 2 | 0.24 | 0.32 | 0.75 | 7.4 | 57 |
| 3 | 0.24 | 0.18 | 1.33 | 10 | 52 |
| 4 | 0.49 | 0.10 | 5 | 2 | >90 |
| 5 | 1.96 | 0.10 | 20 | 2 | >90 |

EXAMPLE II

Five experiments were conducted, using DMB and DCAC, each in a concentration of 0.24 mol/l, and the molar ratios of zinc to DCAC stated in Table II. This table also presents the yields of compound A.

Table II

| Experiment No. | Molar ratio Zn:DCAC | Yield of A, % |
|---|---|---|
| 1 | 1.0 | 17 |
| 2 | 1.1 | 27 |
| 3 | 1.5 | 58 |
| 4 | 2.0 | 62 |
| 5 | 4.0 | 64 |

EXAMPLE III

Five experiments were conducted, using equal molar amounts of DMB and DCAC, a molar ratio of zinc to DCAC of 2 and the concentrations of DCAC stated in Table III. In experiments 4 and 5 the DCAC was admitted over periods of 16 and 24 hours, respectively, instead of 4 hours. Table III also presents the yields of compound A.

Table III

| Experiment No. | Concentration of DCAC, mol/l | Yield of A, % |
|---|---|---|
| 1[1] | 0.24 | 62 |
| 2 | 0.42 | 41 |
| 3 | 0.84 | 38 |
| 4 | 0.42 | 38 |
| 5 | 0.84 | 37 |

[1]same as Example II, experiment 4.

EXAMPLE IV

A mixture of DCAC and DMB (instead of only DCAC) ws added to a stirred mixture of deithyl ether and zinc granules (instead of a mixture of DMB, zinc granules and diethyl ether). Three experiments were conducted in this manner, using a molar ratio of zinc to DCAC to 2 and the molar ratios of DMB to DCAC and the concentrations of DCAC stated in Table IV. This table also presents the yields of compound A.

Table IV

| Experiment No. | Concentration of DCAC, mol/l | Molar ratio DMB:DCAC | Yield of A, % |
| --- | --- | --- | --- |
| 1 | 0.42 | 1.0 | 53 |
| 2 | 0.42 | 1.1 | 52 |
| 3 | 0.84 | 1.0 | 42 |

The yields obtained in experiments 1 and 3 are higher than those of experiments 2 and 3, respectively, of Example III, in which the same concentrations of DCAC were applied.

EXAMPLE V

EXPERIMENT A

One experiment was conducted using a molar ratio of DMB to DCAC of 0.75 and a molar ratio of zinc to DCAC of 7.4. The flask was charged with 400 ml of diethyl ether instead of 1 l. The DCAC was used in an amount of 0.16 mol dissolved in 100 ml of diethyl ether. The reaction mixture was stirred for an additional period of 2 — instead of 8 — hours after the DCAC had been admitted. The yield of compound A was 57%.

EXPERIMENT B (NOT ACCORDING TO THE INVENTION)

A mixture of 50 ml of diethyl ether, 0.012 mol of DCAC and 0.036 mol of zinc granules having a largest dimension of 1 mm was vigorously stirred under reflux at a temperature of 34° C. After 16 hours' stirring the DCAC had fully disappeared. Then, the zinc was removed by decantation and 0.012 mol of DMB was added to the liquid obtained. The mixture thus formed was vigorously stirred for 3 hours at a temperature of 34° C. At the end of this period no detectable amount of cyclobutanone was present in the mixture.

The experiments described in Examples VI-X were conducted as follows, unless otherwise stated.

A three-necked flask was charged with 10 mmol of DCAC, 0.6 mmol of KI, 96 mmol of zinc turnings having a largest dimension of 0.841 mm (20 mesh, U.S. Sieve Series, A.S.T.M.-E-11-61) and 20 ml of a solvent. The initial temperature of the mixture thus formed was 38° C. The mixture was heated to 43° C, stirred for 1 hour and then 48 mmol (5.7 ml) of DMB were added in one portion. Subsequently, 52 mmol of DCAC were admitted over a period of 35 minutes and the reaction mixture thus formed was stirred for a further period of 1.25 hours, at a stirrer speed of 2000 revolutions per minute.

EXAMPLE VI

Six experiments were conducted, using the solvents mentioned in Table VI. This table also presents the yields of compound A, calculated on starting DCAC.

Table VI

| Exp. No. | Solvent | Yield of A, % | Polymer formed | Colour of reaction mixture |
| --- | --- | --- | --- | --- |
| 1 | acetone | 21 | much | dark brown |
| 2 | methyl ethyl ketone | 30 | some | light brown |
| 3 | methyl isobutyl ketone | 38 | some | light brown |
| 4 | diisobutyl ketone | 54 | very little | yellow |
| 5 | methyl tert-butyl ketone | 53 | little | yellow |
| 6 | di-tert-butyl ketone | less than 0.8 | much | dark brown |

The polymers formed in experiments 1 and 2 originated from DCAC and DMB. The DMB that had reacted in experiments 3, 4 and 5 was fully converted into compound A. $ZnCl_2$ formed in experiment 6 on the surface of the zinc particles did not dissolve. The more polymer is formed, the darker the colour of the reaction mixture.

EXAMPLE VII

Four experiments were conducted using diisobutyl ketone as the solvent and the concentrations of DMB and DCAC stated in Table VII. This table also states the molar ratios of DMB to DCAC calculated from these concentrations and presents the yields of compound A.

Table VII

| Experiment No. | Concentration, DMB | Mol/l, of DCAC | Molar ratio DMB:DCAC | Yield of A, % |
| --- | --- | --- | --- | --- |
| 1[1] | 2.4 | 3.1 | 0.78 | 54 |
| 2 | 4.8 | 3.1 | 1.55 | 58 |
| 3 | 12.0 | 3.1 | 3.87 | 56 |
| 4 | 46.5 | 3.1 | 15.0 | 0 |

[1]same as Example IX, experiment 1.

Very little polymer was formed and the DMB that had reacted was fully converted into compound A. The $ZnCl_2$ formed did not fully dissolve in experiment 3 and none of it dissolved in experiment 4.

EXAMPLE VIII

Three experiments were conducted using diisobutyl ketone as the solvent, 62 mmol of DCAC and the molar ratios of zinc to DCAC stated in Table VIII. This table also presents the yields of compound A. The DMB that had reacted was fully converted into compound A.

Table VIII

| Experiment No. | Molar ratio zinc:DCAC | Yield of A, % |
| --- | --- | --- |
| 1 | 1.1 | 51 |
| 2 | 1.55 | 70 |
| 3 | 3.9 | 75 |

EXAMPLE IX

Three experiments were conducted using diisobutyl ketone as the solvent and a molar ratio of DMB to DCAC of 0.78. Table IX states the concentrations in which DMB and DCAC were used and presents the yields of compound A.

Table IX

| Experiment No. | Concentration, DMB | Mol/l, of DCAC | Yield of A, % |
| --- | --- | --- | --- |
| 1[1] | 2.4 | 3.1 | 54 |

Table IX-continued

| Experiment No. | Concentration, DMB | Mol/l, of DCAC | Yield of A, % |
|---|---|---|---|
| 2 | 4.8 | 6.2 | 50 |
| 3 | 9.6 | 12.3 | 37 |

[1]same as example VII, experiment 1.

EXAMPLE X

Three experiments were conducted using diisobutyl ketone as the solvent, at the temperatures stated in Table X. This table also presents the yields of compound A.

Table X

| Ex. No. | Temp., °C | Yield of A, % | Polymer formed | Colour of reaction mixture |
|---|---|---|---|---|
| 1 | 24 | 36 | little | yellow |
| 2 | 43 | 54 | little | yellow |

EXAMPLE XI

An amount of 10.3 mmol of DCAC was added to a stirred suspension of 240 mmol of zinc turnings (same dimensions as in Example VI), 6 mmol of ammonium chloride and 0.6 mmol of potassium iodide in 20 ml of diisobutyl ketone at a temperature of 38° C. The solution turned yellow within 3 minutes, and a rise in temperature was observed. The temperature was kept between 40° C and 45° C. After 10 minutes 96 mmol of 2-methyl-2-pentene were added in one portion. Subsequently, 51.7 mmol of DCAC were added over period of 30 minutes. The mixture was then stirred at a temperature between 40° C and 45° C for 1.25 hours.

The orange-yellow solution thus formed was decanted into a separatory funnel, the excess zinc was washed three times with acetone, the acetone washings were added to the orange-yellow solution and the mixture thus formed was washed with 200 ml of water. Some precipitate was formed, which dissolved after acidifying with some drops of concentrated aqueous hydrochloric acid. The acidified solution — which contained 2-chloro-3-ethyl-4,4-dimethylcyclobutanone and 2-chloro-4-ethyl-3,3-dimethylcyclobutanone, which are novel compounds — was then stirred with 110 ml of a 1 M aqueous sodium hydroxide solution at a temperature of 22° C for 0.75 hour. Then, the mixture was separated into an aqueous and an organic layer. The aqueous layer was acidified with 7.5 ml of concentrated aqueous hydrochloric acid. The oil thus formed was extracted with diethyl ether and the extract phase dried over anhydrous magnesium sulphate. Evaporation of the diethyl ether left 3.8 g of a viscous oil containing 84 %w of 2,2-dimethyl-3-ethylcyclopropane-carboxylic acid. The yield of this novel acid was 42%, calculated on DCAC. The selectivity to this acid was more than 50%. About 60% of this acid had the trans structure.

EXAMPLE XII

An amount of 10.3 mmol of DCAC was added to a stirred suspension of 240 mmol of zinc turnings (same dimensions as in Example VI), 6 mmol of ammonium chloride and 0.6 mmol of potassium iodide in 20 ml of diisobutyl ketone at a temperature of 40° C. The solution turned yellow within 3 minutes, and a rise in temperature was observed. The temperature was kept between 40° C and 45° C. After 8 minutes 96 mmol of 2,5-dimethyl-2,4-hexadiene were added in one portion. Subsequently, 51.7 mmol of DCAC were added over a period of 30 minutes. The mixture was then stirred at a temperature between 40° C and 45° C for 1 hour.

The orange-yellow solution thus formed was decanted into a separatory funnel, the excess zinc was washed three times with acetone, the acetone washings were added to the orange-yellow solution and the mixture thus obtained was washed with 175 ml of water. The washed mixture — which contained the two novel compounds 2-chloro-4,4-dimethyl-3-(2-methyl-1-propenyl)cyclobutanone and 2-chloro-3,3-dimethyl-4-(2-methyl-1-propenyl)cyclobutaone — was stirred with 110 ml of a 1 M aqueous sodium hydroxide solution at a temperature of 22° C for 0.75 hour. Then the mixture was separated into an aqueous and an organic layer. The aqueous layer was acidified with 7.5 ml of concentrated aqueous hydrochloric acid. The oil thus formed was extracted with chloroform and the extract phase dried over anhydrous magnesium sulphate. Evaporation of the chloroform from the extract phase left 5.5 g of a viscous oil containing 70 %w of chrysantemum-monocarboxylic acid. The yield of this acid was 37%, calculated on DCAC. About 96% of this acid had the trans structure.

EXAMPLE XIII

An amount of 10.3 mmol of DCAC was added to a stirred suspension of 240 mmol of zinc turnings (same dimensions as in Example VI), 6 mmol of ammonium chloride and 0.6 mmol of potassium iodide in 20 ml of diisobutyl ketone at a temperature of 40° C. The temperature was kept between 40° C and 45° C. After 3 minutes 48 mmol of isopropyl 3-methyl-2-butenyl ether were added in one portion. Subsequently, 51.7 mmol of DCAC were added over a period of 20 minutes. The mixture was then stirred at a temperature between 40° C and 45° C for 0.25 hours.

The yellow solution thus formed was decanted into a separatory funnel, the excess zinc was washed three times with acetone, the acetone washings were added to the yellow solution and the mixture thus obtained was washed with 175 ml of water. The washed mixture — which contained the two novel compounds 2-chloro-4-isopropoxymethyl-3,3-di-methylcyclobutanone and 2-chloro-3-isopropoxymethyl-4,4-dimethylcyclobutanone — was stirred with 110 ml of a 1 M aqueous sodium hydroxide solution at a temperature of 22° C for 0.75 hour. Then, the mixture was separated into an aqueous and an organic layer. The aqueous layer was acidified with 7.5 ml of concentrated aqueous hydrochloric acid. The oil thus formed was extracted with chloroform and the extract phase dried over anhydrous magnesium sulphate. Evaporation of the chloroform from the extract phase left 2.65 g of a viscous oil containing 64 %w of 2,2-dimethyl-3-isopropoxymethylcyclopropanecarboxylic acid. The yield of this novel acid was 15%, calculated on DCAC. About two thirds of this acid had the trans structure.

EXAMPLE XIV

An amount of 51.7 mmol of DCAC was added to a stirred suspension of 1200 mmol of zinc turnings (same dimensions as in Example VI), 29.9 mmol of ammonium chloride and 3.0 mmol of potassium iodide in 100 ml of diisobutyl ketone at a temperature of 35° C. The solution turned yellow within 5 minutes, and a rise in temperature was observed. The temperature was kept between 40° C and 45° C. After 5 minutes 240 mmol of benzyl 3-methyl-2-butenyl ether were added in one portion, resulting in a temperature rise to 50° C. Ten minutes after the addition of the benzyl 3-methyl-2-butenyl ether 310 mmol of DCAC were added over a period of 35 minutes. The mixture was then stirred at a temperature between 40° C and 45° C for 0.75 hour.

The solution thus formed was decanted into a separatory funnel, the excess zinc was washed three times with acetone, the acetone washings were added to the solution and the mixture thus obtained was washed with 500 ml of water. The washed mixture — which contained the two novel compounds 2-benzyloxymethyl-4-chloro-3,3-dimethylcyclobutanone and 3-benzyloxymethyl-2-chloro-4,4-dimethylcyclobutanone — was stirred with 550 ml of a 1 M aqueous sodium hydroxide solution at a temperature of 22° C for 0.75 hour. Then, the mixture was separated into an aqueous and an organic layer. The aqueous layer was acidified with 40 ml of concentrated aqueous hydrochloric acid. The oil thus formed was extracted with chloroform and the extract phase dried over anhydrous magnesium sulphate. Evaporation of the chloroform from the extract phase left 14.0 g of a viscous oil containing 53 %w of the novel compound 2-benzyloxymethyl-3,3-dimethylcyclopropanecarboxylic acid. The yield of this acid was 8%, calculated on DCAC. About 57% of this acid had the trans structure.

EXAMPLE XV

A three-necked flask was charged with 10 ml of diethyl ether, 3 mmol of an unsaturated compound and 6 mmol of zinc granules and kept with stirring at a temperature of 35° C. Then, 6 mmol of DCAC were added in one portion. Seven experiments were conducted, each with another unsaturated compound. Table XI indicates what unsaturated compounds were used and presents the yields of the cyclic compounds formed, calculated on DCAC, at various moments after the start of the experiment. The cyclic compounds formed — except 2-chloro-3,3,4,4-tetramethylcyclobutanone — are novel.

Table XI

| Unsaturated compound | Cyclic compounds formed | Yield of cyclic compounds, after ... min., % | | | | |
|---|---|---|---|---|---|---|
| | | 15 | 30 | 60 | 120 | 180 |
| Propene | 2-Chloro-4-methylcyclobutanone and 2-chloro-3-methylcyclobutanone | 28 | 34 | | | 35 |
| Cis-2-butene | 2-Chloro-3,4-dimethylcyclobutanone | 12 | | 39 | 43 | 43 |
| Trans-2-butene | 2-Chloro-3,4-dimethylcyclobutanone | 45 | 53 | | | 54 |
| Isobutene | 2-Chloro-4,4-dimethylcyclobutanone and 2-chloro-3,3-dimethylcyclobutanone | 10 | 21 | | 49 | 51 |
| 2-Methyl-2-butene | 2-Chloro-3,4,4-trimethylcyclobutanone and 2-chloro-3,3,4-trimethylcyclobutanone | 50 | 55 | | 55 | 67 |
| 2,3-Dimethyl-2-butene | 2-Chloro-3,3,4,4,-tetramethylcyclobutanone | 43 | 59 | 67 | | 36 |
| 2-Butyne | 4-Chloro-2,3-dimethylcyclobuten-2-one | 29 | 35 | | | |

EXAMPLE XVI

A three-necked flask was charged with 1 l of dried diethyl ether, 0.54 mol of zinc granules having a largest dimension of 1 mm and 0.24 mol of 2,3-dimethyl-2-butene. The suspension in the flask was kept boiling under reflux and a solution of 0.24 mol of DCAC in 50 ml of dried diethyl ether was admitted dropwise from the dosage funnel over a period of 4 hours. The reaction mixture thus formed was stirred under reflux for an additional period of 8 hours. After cooling to a temperature of 20° C, the reaction mixture was washed with an equal volume of water. The two phases were separated and the organic layer obtained — containing compound A — was stirred with a solution of 0.5 mol of sodium hydroxide in 500 ml of water and while stirring the diethyl ether was distilled off. Then, consecutively, 20 %w aqueous hydrochloric acid was added to the residue obtained until the pH reached a value of 2.5, the solution was subjected to steam distillation and the distillate was separated by filtration into an aqueous liquid and solid 2,2,3,3-tetramethylcyclopropanecarboxylic acid. The yield of this acid was 57%, calculated on DCAC.

EXAMPLE XVII

The procedure described in Example XVI was repeated with four other ethylenically unsaturated compounds. Table XII states the unsaturated compounds used and presents the names of the cyclobutanones and cyclopropanecarboxylic acids formed, the yields in which these compounds were obtained and some physical data of these compounds.

Table XII

| Unsaturated compound | Cyclobutanone formed | | Cyclopropanecarboxylic acid formed | | Physical data |
|---|---|---|---|---|---|
| | Name | Yield, % | Name | Yield, % | |
| 2,4-dimethyl-2,3-pentadiene | 2-chloro-4,4-dimethyl-3-isopropylidenecyclobutanone* and 4-chloro-3,3-dimethyl-2-isopropylidenecyclobutanone | 30 | 2,2-dimethyl-3-isopropylidenecyclopropanecarboxylic acid | 23 | boiling point 70° C/10 mm |
| 2,5-dimethyl-2,4-hexadiene | 2-chloro-4,4-dimethyl-3-(2-methyl-1-propenyl)cyclobutanone* and 2-chloro-3,3-dimethyl-4-(2-methyl-1-propenyl)cyclobutanone* | 42 | 2,2-dimethyl-3-(2-methyl-1-propenyl)-cyclopropanecarboxylic acid (chrysanthemum-monocarboxylic acid) | 25 | melting point 53° C |
| ethyl 2,3,5-trimethyl-2,4-hexadienoate | 2-chloro-3,3-dimethyl-4-(1-methyl-2-ethoxycarbonyl-1-propenyl)cyclobutanone*; 2-chloro-4,4-dimethyl-3- | 38 | 2-(1-methyl-2-carboxy-1-propenyl)-3,3-dimethylcyclopropanecarboxylic acid* and | 14 | |

Table XII-continued

| Unsaturated compound | Cyclobutanone formed Name | Yield, % | Cyclopropanecarboxylic acid formed Name | Yield, % | Physical data |
|---|---|---|---|---|---|
| | (1-methyl-2-ethoxycarbonyl-1-propenyl)cyclobutanone*; 2-chloro-3,4-dimethyl-3-ethoxycarbonyl-4-(2-methyl-propenyl)cyclobutanone*,and 2-chloro-3,4-dimethyl-4-ethoxycarbonyl-3-(2-methyl-propenyl)cyclobutanone*. | | isomers thereof | | |
| 1,2-dimethyl-cyclopentene | 6-chloro-1,4-dimethylbi-cyclo[3.2.0]heptanone-5* (endo and exo) | 20 | 1,5-dimethylbicyclo-[3.1.0]hexane-6-carboxylic acid* | 12 | melting point 62° C |

*This compound is novel.

EXAMPLE XVIII

The procedure described in Example XVI was repeated with 0.5 mol of tin powder instead of 0.5 mol of zinc granules. Compound A was obtained in a yield of 25%.

What we claim is:

1. A process for the preparation of a cyclobutanone which process comprises contacting a 2-haloacyl halide of the formula

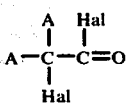

in which formula each A represents a halogen atom having an atomic number of not more than 35, a hydrogen atom or an unsubstituted hydrocarbyl group; and each Hal represents a halogen atom having an atomic number of not more than 35, in an alkanone solvent which has at least two branches in the carbon skeleton of the molecule and of which not more than one of the carbon atoms attached to the carbonyl group is quaternary with a straight or branched chain alkene having from 2 to about 20 carbon atoms at a temperature above 5° C in the presence of zinc and/or tin.

2. A process as claimed in claim 1, in which the 2-haloacyl halide is a 2,2-dihaloacyl halide.

3. A process as claimed in claim 2, in which the 2,2-dihaloacyl halide is dichloroacetyl chloride.

4. A process as claimed in claim 1, in which the alkene is 2,3-dimethyl-2-butene, 2-methyl-2

5. A process as claimed in claim 1, in which diisobutyl ketone or methyl tert-butyl ketone is used as the solvent.

6. A process as claimed in claim 1, in which the 2-haloacyl halide is applied in a concentration in the range of from 1 to 15 mol per liter of the ketone.

7. A process as claimed in claim 6 wherein the concentration is in the range of from 3 to 10 mol per liter.

8. A process as claimed in claim 1, in which the molar ratio of alkene to 2-haloacyl halide is in the range of from 0.5 to 10.

9. A process as claimed in claim 8 wherein the molar ratio is in the range of from 1 to 2.

10. A process as claimed in claim 1, in which the molar ratio of zinc or tin to 2-haloacyl halide is in the range of from 1 to 10.

11. A process as claimed in claim 10 wherein the molar ratio is in the range of from 1 to 5.

12. A process as claimed in claim 1, which is conducted at a temperature in the range of from 25° C to 60° C.

13. A process as claimed in claim 12 wherein the temperature is in the range of from 35° C to 50° C.

14. A process as claimed in claim 1, which is conducted by gradually adding the 2-haloacyl halide to a homogeneous distribution of zinc or tin in an alkene.

15. A process as claimed in claim 14, in which a suspension of zinc or tin in a solvent containing less than 25% of the total amount of the 2-haloacyl halide to be used is stirred and the alkene and subsequently the balance of the 2-haloacyl halide are added to the stirred suspension.

16. A process as claimed in claim 1, which is conducted in the presence of 0.1 to 10% mol of an inorganic halide catalyst selected from mercuric iodide, sodium chloride, potassium iodide and ammonium chloride, calculated on 2-haloacyl halide.

17. A process as claimed in claim 16, which is conducted in the presence of potassium iodide and/or ammonium chloride.

* * * * *

UNITED STATES PATENT AND TRADEMARK OFFICE
CERTIFICATE OF CORRECTION

PATENT NO. : 4,028,418
DATED : June 7, 1977
INVENTOR(S) : VAN DEN BRINK, AUSTERMÜHLE-BERTOLA, KRAMER It is certified that error appears in the above-identified patent and that said Letters Patent are hereby corrected as shown below:

Claim 4, line 2, change "2-methyl-2" to -- 2-methyl-2-pentene --.

Signed and Sealed this thirtieth Day of August 1977

[SEAL]

Attest:

RUTH C. MASON
Attesting Officer

C. MARSHALL DANN
Commissioner of Patents and Trademarks